United States Patent
Blumer et al.

(10) Patent No.: US 12,192,707 B2
(45) Date of Patent: *Jan. 7, 2025

(54) CUSTOMIZABLE EAR INSERT

(71) Applicant: Logitech Europe S.A., Lausanne (CH)

(72) Inventors: Daniel Blumer, Cote St Luc (CA); Navi Cohen, Sunnyvale, CA (US)

(73) Assignee: Logitech Europe S.A., Lausanne (CH)

( * ) Notice: Subject to any disclaimer, the term of this patent is extended or adjusted under 35 U.S.C. 154(b) by 171 days.

This patent is subject to a terminal disclaimer.

(21) Appl. No.: 17/826,095

(22) Filed: May 26, 2022

(65) Prior Publication Data

US 2022/0286794 A1    Sep. 8, 2022

Related U.S. Application Data

(63) Continuation of application No. 16/263,478, filed on Jan. 31, 2019, now Pat. No. 11,375,326, which is a
(Continued)

(51) Int. Cl.
*H04R 25/00* (2006.01)
*A61F 11/08* (2006.01)
(Continued)

(52) U.S. Cl.
CPC ............ *H04R 25/554* (2013.01); *A61F 11/08* (2013.01); *A61F 11/10* (2013.01); *H04R 1/1016* (2013.01);
(Continued)

(58) Field of Classification Search
CPC .. H04R 1/1016; H04R 1/1058; H04R 1/1075; H04R 25/60; H04R 25/609;
(Continued)

(56) References Cited

U.S. PATENT DOCUMENTS

| 2,535,258 A | 12/1950 | Bland |
| 3,440,314 A | 4/1969 | Frisch |

(Continued)

FOREIGN PATENT DOCUMENTS

| CN | 101919272 A | 12/2010 |
| CN | 102473407 A | 5/2012 |

(Continued)

OTHER PUBLICATIONS

Extended European Search Report mailed Nov. 13, 2017 in European Patent Application No. 15799822.0 (European Publication No. ), pages.
(Continued)

*Primary Examiner* — Sunita Joshi
(74) *Attorney, Agent, or Firm* — Patterson + Sheridan, LLP

(57) ABSTRACT

The present invention provides a customizable ear insert for fitting within a user's outer ear or ear canal or both and methods therefor. In accordance with an aspect of the present invention, there is provided a customizable ear insert having: a body formed of photocurable polymer, the body having a first shape configured for insertion into the outer ear canal of a user; a light source, the light source positioned adjacent the body, and wherein the body can be cured into a second shape by application of light generated by the light source, the second shape snugly conforming to the interior surface of the user's outer ear or ear canal or both.

20 Claims, 3 Drawing Sheets

Related U.S. Application Data continuation of application No. 15/109,104, filed on Jun. 29, 2016, now Pat. No. 10,251,789.

(60) Provisional application No. 62/005,276, filed on May 30, 2014.

(51) Int. Cl.
| | | |
|---|---|---|
| *A61F 11/10* | (2006.01) | |
| *H04R 1/10* | (2006.01) | |
| *H04R 25/02* | (2006.01) | |
| *A61F 11/14* | (2006.01) | |

(52) U.S. Cl.
CPC ............ *H04R 25/60* (2013.01); *A61F 11/085* (2022.01); *A61F 11/145* (2022.01); *H04R 1/1058* (2013.01); *H04R 1/1075* (2013.01); *H04R 25/02* (2013.01); *H04R 25/305* (2013.01); *H04R 25/456* (2013.01); *H04R 25/604* (2013.01); *H04R 25/609* (2019.05); *H04R 2225/025* (2013.01); *H04R 2225/55* (2013.01); *H04R 2420/09* (2013.01); *H04R 2460/15* (2013.01)

(58) Field of Classification Search
CPC .... H04R 25/554; H04R 25/02; H04R 25/456; H04R 2420/09; H04R 2225/55
See application file for complete search history.

(56) References Cited

U.S. PATENT DOCUMENTS

| | | | |
|---|---|---|---|
| 3,475,528 | A | 10/1969 | Parks |
| 4,163,877 | A | 8/1979 | Schonstedt |
| 4,657,106 | A | 4/1987 | Hardt |
| 4,712,245 | A | 12/1987 | Lyregaard |
| 4,800,636 | A | 1/1989 | Topholm |
| 4,834,211 | A | 5/1989 | Bibby et al. |
| 4,834,927 | A | 5/1989 | Birkholz et al. |
| 4,962,537 | A | 10/1990 | Basel et al. |
| 5,185,802 | A | 2/1993 | Stanton |
| 5,321,757 | A | 6/1994 | Woodfill, Jr. |
| 5,333,622 | A | 8/1994 | Casali et al. |
| 5,455,994 | A | 10/1995 | Termeer et al. |
| 5,530,763 | A | 6/1996 | Aebi et al. |
| 5,631,965 | A | 5/1997 | Chang et al. |
| 5,804,109 | A | 9/1998 | Perkins |
| 6,310,961 | B1 | 10/2001 | Oliveira et al. |
| 6,401,859 | B1 | 6/2002 | Widmer et al. |
| 6,427,018 | B1 | 7/2002 | Keliiliki |
| 6,432,247 | B1 | 8/2002 | Juneau et al. |
| 6,772,853 | B2 | 8/2004 | Yang |
| 6,829,365 | B1 | 12/2004 | Kim |
| 7,116,795 | B2 | 10/2006 | Tuason et al. |
| 7,231,056 | B2 | 6/2007 | Chen |
| 7,251,335 | B1 | 7/2007 | Chen |
| 7,317,806 | B2 | 1/2008 | Harvey et al. |
| 7,489,794 | B2 | 2/2009 | Harvey |
| 7,499,562 | B2 | 3/2009 | Shim |
| 7,634,099 | B2 | 12/2009 | Harvey et al. |
| D628,990 | S | 12/2010 | Pedersen |
| 7,858,897 | B2 | 12/2010 | Beranger |
| D630,621 | S | 1/2011 | Pedersen |
| D634,306 | S | 3/2011 | Pedersen |
| 7,971,338 | B2 | 7/2011 | Yang et al. |
| 7,991,179 | B2 | 8/2011 | Drambarean et al. |
| 8,194,911 | B2 | 6/2012 | Dyer et al. |
| 8,515,115 | B2 | 8/2013 | Kelly et al. |
| 8,630,436 | B2 | 1/2014 | Berg |
| 8,666,102 | B2 | 3/2014 | Bruckhoff et al. |
| 8,682,001 | B2 | 3/2014 | Annunziato et al. |
| 8,815,115 | B2 * | 8/2014 | Coda ............... F24S 40/46 423/248 |
| 8,841,603 | B1 | 9/2014 | Blanton et al. |
| 8,897,458 | B2 | 11/2014 | Parkins et al. |
| 8,900,125 | B2 | 12/2014 | Berglund et al. |
| 8,900,127 | B2 | 12/2014 | Berglund et al. |
| 8,900,128 | B2 | 12/2014 | Berglund et al. |
| 8,900,129 | B2 | 12/2014 | Berglund et al. |
| 8,900,130 | B2 | 12/2014 | Berglund et al. |
| 8,976,995 | B2 | 3/2015 | Berg |
| 9,002,023 | B2 | 4/2015 | Gauger, Jr. |
| 9,042,589 | B2 | 5/2015 | Depallens et al. |
| 9,191,758 | B2 | 11/2015 | Depallens et al. |
| D744,456 | S | 12/2015 | Pedersen |
| D773,440 | S | 12/2016 | Pedersen |
| D773,441 | S | 12/2016 | Pedersen |
| D774,021 | S | 12/2016 | Pedersen |
| 10,021,496 | B2 | 7/2018 | Clausen et al. |
| 10,034,105 | B2 | 7/2018 | Higgins et al. |
| 10,158,933 | B2 | 12/2018 | Prevoir et al. |
| 10,284,975 | B2 | 5/2019 | Higgins et al. |
| 2003/0000706 | A1 | 1/2003 | Carstensen |
| 2006/0133636 | A1 | 6/2006 | Harvey et al. |
| 2006/0159279 | A1 | 7/2006 | Kuo et al. |
| 2006/0188119 | A1 | 8/2006 | Parker |
| 2006/0281502 | A1 | 12/2006 | Chang et al. |
| 2007/0036385 | A1 | 2/2007 | Harvey et al. |
| 2008/0044034 | A1 | 2/2008 | Hou |
| 2008/0119244 | A1 | 5/2008 | Malhotra |
| 2009/0173353 | A1 | 7/2009 | Purcell et al. |
| 2009/0233652 | A1 | 9/2009 | Yang |
| 2009/0279731 | A1 | 11/2009 | Wu |
| 2010/0019417 | A1 | 1/2010 | Chua et al. |
| 2010/0278364 | A1 | 11/2010 | Berg |
| 2011/0002491 | A1 * | 1/2011 | Klemenz ............. H04R 25/658 381/322 |
| 2011/0058702 | A1 | 3/2011 | Saggio, Jr. |
| 2011/0159229 | A1 | 6/2011 | Doehle et al. |
| 2011/0228963 | A1 | 9/2011 | Goldstein et al. |
| 2012/0028107 | A1 | 2/2012 | Sugita et al. |
| 2012/0237068 | A1 | 9/2012 | Fretz et al. |
| 2013/0202141 | A1 | 8/2013 | Basseas |
| 2013/0243209 | A1 | 9/2013 | Zurbruegg et al. |
| 2013/0251186 | A1 | 9/2013 | Matsuo et al. |
| 2013/0269448 | A1 | 10/2013 | Berger et al. |
| 2013/0294634 | A1 | 11/2013 | Chen |
| 2014/0003644 | A1 | 1/2014 | Keady et al. |
| 2014/0105431 | A1 | 4/2014 | Berg |
| 2014/0313506 | A1 | 10/2014 | Bergman et al. |
| 2015/0038850 | A1 | 2/2015 | Tatzilias et al. |
| 2015/0038871 | A1 | 2/2015 | Hatzilias et al. |
| 2015/0038880 | A1 | 2/2015 | Hatzilias et al. |
| 2015/0039087 | A1 | 2/2015 | Hatzilias et al. |
| 2015/0057533 | A1 | 2/2015 | Bergman et al. |
| 2015/0067929 | A1 | 3/2015 | Blanton et al. |
| 2015/0097929 | A1 | 4/2015 | Bergman et al. |
| 2015/0097931 | A1 | 4/2015 | Hatzilias et al. |
| 2015/0097935 | A1 | 4/2015 | Hatzilias et al. |
| 2015/0097968 | A1 | 4/2015 | Bergman et al. |
| 2015/0098636 | A1 | 4/2015 | Bergman et al. |
| 2015/0099981 | A1 | 4/2015 | Cahall et al. |
| 2015/0099983 | A1 | 4/2015 | Hatzilias et al. |
| 2015/0190043 | A1 | 7/2015 | Hatzilias |
| 2015/0215693 | A1 | 7/2015 | Sandanger |
| 2015/0281822 | A1 | 10/2015 | Berg |
| 2015/0312665 | A1 | 10/2015 | Berg |
| 2015/0374480 | A1 | 12/2015 | Grewe |
| 2016/0051134 | A1 | 2/2016 | Hatzilias |
| 2016/0205456 | A1 | 7/2016 | Berg |
| 2016/0317352 | A1 | 11/2016 | Blumer et al. |
| 2017/0134844 | A1 | 5/2017 | Liu et al. |
| 2017/0311069 | A1 | 10/2017 | Prevoir et al. |
| 2018/0332379 | A1 | 11/2018 | Mcgarry et al. |
| 2019/0253783 | A1 | 8/2019 | O'Callaghan |

FOREIGN PATENT DOCUMENTS

| | | |
|---|---|---|
| CN | 102655717 A | 9/2012 |
| CN | 103269466 A | 8/2013 |
| CN | 103384356 A | 11/2013 |
| CN | 203587922 U | 5/2014 |
| CN | 204518015 U | 7/2015 |

(56) References Cited

FOREIGN PATENT DOCUMENTS

| | | |
|---|---|---|
| EP | 0498592 A2 | 8/1992 |
| EP | 1116414 A1 | 7/2001 |
| EP | 2268063 A1 | 12/2010 |
| EP | 3188510 A1 | 7/2017 |
| JP | S63276398 A | 11/1988 |
| JP | 2008236147 A | 10/2008 |
| WO | 01/43495 A2 | 6/2001 |
| WO | 2005/125280 A2 | 12/2005 |
| WO | 2011022358 A1 | 2/2011 |
| WO | 2012/129229 A2 | 9/2012 |
| WO | 2013/138078 A2 | 9/2013 |
| WO | 2013/138079 A3 | 9/2013 |
| WO | 2015/030861 A1 | 3/2015 |
| WO | 2015/030862 A1 | 3/2015 |
| WO | 2015/179975 A1 | 12/2015 |

OTHER PUBLICATIONS

Australian action dated Oct. 15, 2018 for Application No. 2015268066.
International Search Report PCT/CA2015/050479.
International Preliminary Report PCT/CA2015/050479.
Chinese First Office Action dated Aug. 31, 2018 for Application No. 201580041252.1.
International Search Report dated Mar. 6, 2019 for Application No. PCT/IB2019/050035.
CN Office Action dated Jun. 8, 2020 for Application No. 201910585968.8.

\* cited by examiner

CUSTOMIZABLE EAR INSERT

CROSS-REFERENCE TO RELATED APPLICATIONS

This application is a continuation application of U.S. patent application Ser. No. 16/263,478, filed Jan. 31, 2019, which is a continuation application of U.S. patent application Ser. No. 15/109,104, filed May 27, 2015, which is a National Stage Entry of PCT/CA2015/050479 filed May 27, 2015 and claims benefit of priority from U.S. Provisional Patent Application Ser. No. 62/005,276, filed May 30, 2014, the entire contents of which are incorporated herein by reference.

FIELD

The present invention pertains to the field of wearable technology and in particular to custom moldable ear inserts for use in a wide variety of applications.

BACKGROUND

Custom-fit earpieces allow for a better fit of the earpiece in one's ear. A custom earpiece's superior noise-suppression can diminish all or at least significant levels of background noise and thereby can increases the prominence of the sounds that the user is trying to listen to and protect the user from potentially dangerous environmental sounds. If a custom fit earpiece is used as an earphone, with less environmental noise overpowering the subtle/quiet details in the music, the user is able to listen at lower volume levels which can result in a safer user experience. More specifically, custom fit earpieces can offer less risk of injury in ear drums as the volume levels can remain lower, and the provided superior fit and increased comfort level can allow for a user to listen for a longer period of time without incurring injury.

The two primary problems associated with custom-fit earpieces are production cost, and the fitting process. For example, the cost for an average pair of custom earphones is currently beyond the earphone budget set aside by most consumers. In addition, custom earpieces generally require the consumer to visit an audiologist to make impressions of the ear canals which incurs additional cost and time.

Therefore there is a need for a customizable ear insert providing high audial performance and provided at a lower economic price point than current industry standards.

This background information is provided to reveal information believed by the applicant to be of possible relevance to the present invention. No admission is necessarily intended, nor should be construed, that any of the preceding information constitutes prior art against the present invention.

BRIEF SUMMARY

It is contemplated that the present invention can provide a customizable ear insert In at least one embodiment, a customizable ear insert for insertion into the outer ear or ear canal or both of a user is provided having a body formed of photocurable polymer, the body having a first shape configured for insertion into the outer ear or ear canal or both, a light source, the light source positioned adjacent the body, and wherein the body can be cured into a second shape by application of light generated by the light source, the second shape snugly conforming to the interior surface of the outer ear or ear canal or both.

In another embodiment, the present invention provides a method of calibrating a photocurable customizable ear insert for fit within the outer ear or ear canal or both of a user, the method having the steps of receiving information from one or more feedback modules via a communication means, comparing the information to a database with predetermined calibration values, outputting instructions to the customizable ear insert components for implementation wherein implementation comprises at least curing the photocurable customizable ear insert into a second shape by application of light generated by a light source, the second shape snugly conforming to the interior surface of the outer ear or ear canal or both.

BRIEF DESCRIPTION OF THE FIGURES

Embodiments of the present invention will be better understood in connection with the following Figures, in which.

DETAILED DESCRIPTION OF THE EMBODIMENTS

Definitions

Figure 1:
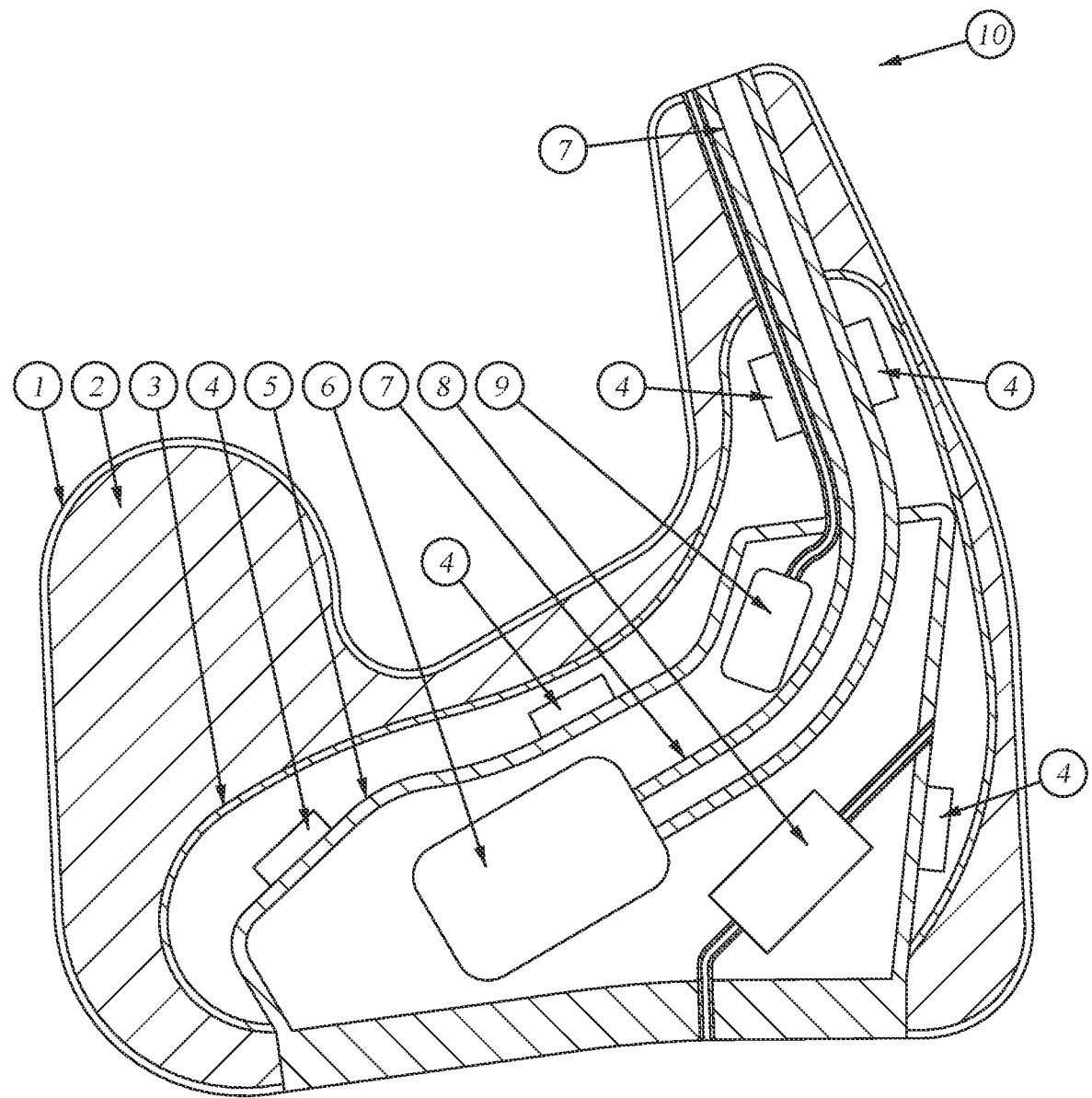
FIG. 1 illustrates a side cutaway view of one embodiment of a customizable ear piece in accordance with the present invention.

As used herein, the term "device" beyond its ordinary meaning, can be defined as any apparatus capable of network access. The device may be wired or wireless. In at least one embodiment, the device may include a personal computer, tablet, mobile device, mobile phone, television, music player, personal organizer, or any similar electronic network enabled device. In at least one embodiment, the device may be wearable technology with network enablement including, but not limited to, jewelry, watches, glasses, hats, clothing, shoes, socks and similar wearable technology reasonably contemplated by one skilled in the art. In at least one embodiment, the device may be a corporately owned personal computer, tablet, mobile device, mobile phone, personal organizer, or any similar electronic network enabled device.

As used herein, the term "App" can be defined as an Application implemented on a device. The Application may be downloaded and locally installed on the device with minimal retrieval of extraneous data from an external network. In at least one embodiment, the Application is a "thin client" on the device and retrieves substantial amounts of information from an external network. In at least one embodiment, the Application is accessed through a network client (e.g., web browser, third party aggregator application). In at least one embodiment, the implementation of the Application may include a hybrid of conventional paradigms such as those described above.

As used herein, the term "communication means", beyond its ordinary meaning, can be defined as any means between the ear piece and the device or any other third party receiving mechanism allowing for signal reception and/or data packet reception. In at least one embodiment, the communication means may be digital and include any necessary elements of hardware, including but not limited to communications ports, wireless transmitter/receivers, wires or fiber optics; and software, including but not limited to telephony, e-mail, facsimile, Bluetooth®, NFC, TCP/IP, FTP, XML, and IRC, that allow a device to exchange data packets with another device. In at least one embodiment, the communication means include USB connectivity, Apple® Lightning cable, Fire wire, Ethernet, auxiliary cable, and similar connectivity standard readily known by the skilled person.

As used herein, the term "about" refers to a +/−10% variation from the nominal value. It is to be understood that such a variation is always included in a given value provided herein, whether or not it is specifically referred to.

Unless defined otherwise, all technical and scientific terms used herein have the same meaning as commonly understood by one of ordinary skill in the art to which this invention belongs.

Customizable Ear Insert Overview

In at least one embodiment, the present invention provides a customizable ear insert which may be utilized for any number of applications for which custom ear inserts provide utility such as ear plugs, hearing aids, headphones, earphones, and other types of applications, as will be readily understood by a person skilled in the art.

In at least one embodiment, the customizable ear insert may utilize a photopolymer such that the ear insert can be photo-cured into a customized fit within the user's outer ear or ear canal or both.

One embodiment of a customizable ear insert (10) in accordance with the present invention is illustrated in FIG. 1. In this embodiment, an outer sleeve (1) surrounds the exterior of customizable ear insert (10). A settable resin forms the body (2) of customizable ear insert (10). In at least one embodiment, it is contemplated that the settable resin is a photocurable polymer, however other arrangements are also contemplated that will be readily appreciated by the skilled person.

In at least one embodiment, a gas-containing chamber can be provided that acts as a bladder (3) to expand and contract to improve the fit within the user's outer ear or ear canal or both. An internal cavity (5), can further be seen which can house optional equipment such as, for example, at least one speaker (6), at least one sound bore (7), a micropump in fluid communication with the bladder (3), and at least one microphone (9), as required by the particular embodiment of the present invention. Further, it is contemplated that at least one embedded light source (4) can be stored in body (2) or cavity (5) or elsewhere (see FIG. 2) depending on the needs and particular configuration of the instant application.

Figure 2:
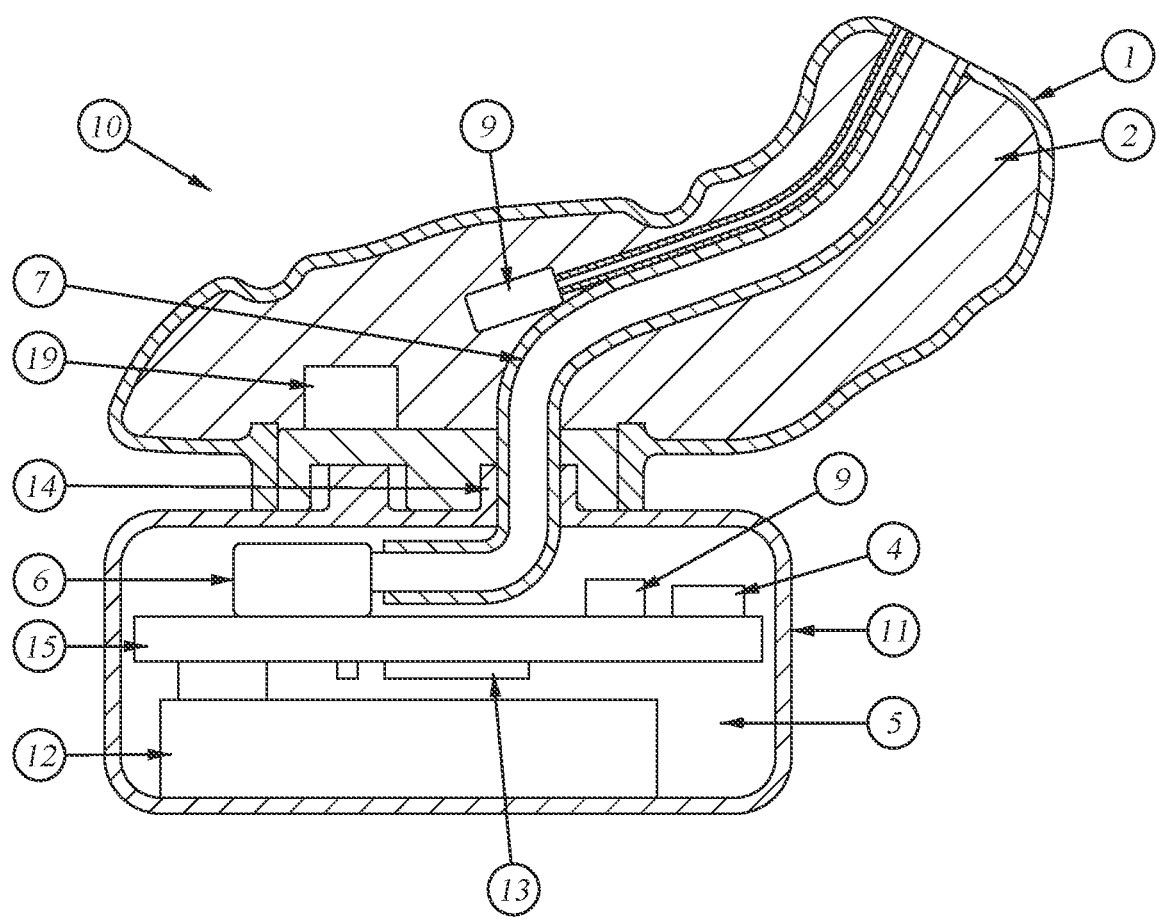
FIG. 2 illustrates a side cutaway view of another embodiment of a customizable ear piece in accordance with the present invention.

Another embodiment of customizable ear insert (10) is illustrated in FIG. 2. In this embodiment, an outer sleeve (1) surrounds a settable resin that forms body (2) of the ear piece. Sleeve (1) and/or body (2) can have an integrated mechanical attachment means (14), which can include, for example, a clip, press fit connection, snap fit connection, among any other suitable arrangement, thereby allowing sleeve (1) and body (2) to be mechanically and removably connected to a housing (11).

In this embodiment, housing (11) can optionally contain at least one speaker (6), at least one light source (4), at least one microphone (9), a battery (12), and an integrated circuit (such as, but not limited to, a chip for wireless (i.e.: Bluetooth) communication) (13). At least one sound bore (7) can also be provided that fluidly communicates with either the at least one speaker (6) or the at least one microphone (9) in order to conduct the sound through the body (2) and sleeve (1) and thereby directing the sound into the user's ear canal. In other embodiments it is contemplated that the at least one sound bore (7) can also be provided that fluidly communicates with either the at least one speaker (6) or the at least one microphone (9) in order to conduct the sound through the body (2) and sleeve (1) and thereby directing the sound to the external environment Finally, and as can be seen in FIG. 3, in some embodiments it is contemplated that in some embodiments sleeve (1) has at least one groove (14) that can improve the fit and operation of customizable ear insert (10) within the user's outer ear, ear canal or both.

Body Component Overview

Figure 3:
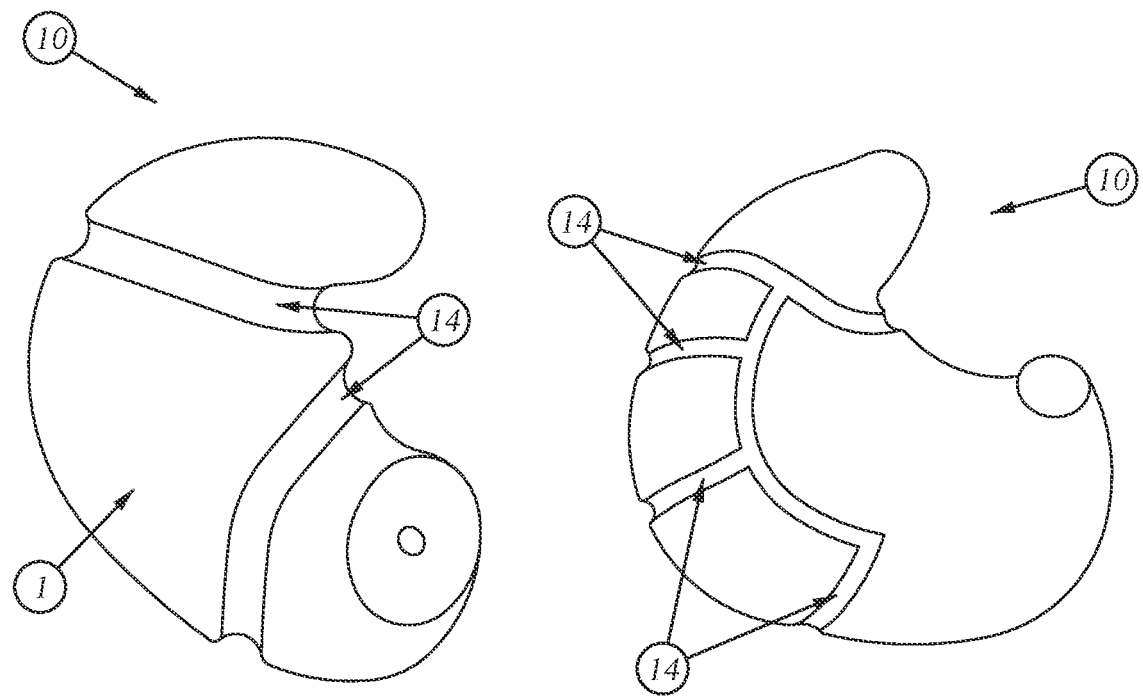
FIG. 3 illustrates perspective views of different embodiments of a customizable ear piece in accordance with the present invention.

It is contemplated that customizable ear insert (10) may be constructed in a number of configurations as seen in FIGS. 1, 2 and 3. In at least one embodiment, the construction of customizable ear insert (10) provides for body (2) to be fitted within the user's outer ear or ear canal or both. Body (2) may be constructed from any material such that the required rigidity characteristics are maintained. In at least one embodiment and as discussed above, it is contemplated that body (2) may be constructed from a photopolymer material. In these embodiments, it is contemplated that the polymer may have varied malleability characteristics pre- and post-photo curing. Further, it is contemplated the photopolymer may be cured using any form of electromagnetic spectrum such as, but not limited to, visible light, ultraviolet light, fluorescent light, among other segments of spectrum readily understood by the skilled person.

In at least one embodiment, body (2) is made from a photopolymer-type material such that the malleability is deformable and pliable such that body (2) may be able to change its form according to the pressures exerted on its outer surface. It is contemplated that body (2) may be inserted into a user's outer ear or ear canal or both such that the deformable properties of body (2) may contour to the internal shape of the user's outer ear or ear canal or both within a prescribed deformability. The pliability of body (2) may be altered depending on application.

For example, smaller bodies made for children may require more deformable specifications. In at least one embodiment, it is contemplated that body (2) is constructed using modified urethane with a specification property of 4,500 centipoise, however other arrangements will be readily appreciated by the skilled person.

As will be readily appreciated by the skilled person, it is contemplated that body (2) may comprise one of, or a combination of: acrylates, methacrylates, urethane acrylates, and urethane methacrylates, among other suitable materials that will be readily appreciated by the skilled person. In at least one embodiment, it is contemplated that the viscosity can range from 30-5,000 centipoise.

In at least one embodiment, the shape of body (2) is constructed such that the shape of body (2) contours to a large percentage of human ears. Ergonomic and anatomic models and knowledge may be used in the construction of body (2) such that the shape of body (2) facilitates intuitive placement into a user's outer ear or ear canal or both.

In at least one embodiment, sleeve (1) is affixed to body (2) such that the malleable body (2) is contained by sleeve (1). In at least one embodiment, body (2) contains a flexible outer shell which functions to hold the body's internal composition intact during the pre-curing process. Sleeve (1) may be affixed to the outer shell either during the curing process or post-curing process.

In at least one embodiment, body (2) is constructed of a gel-like material and is contained within sleeve (1). It is contemplated that the shape of sleeve (1) has elements that are designed to fit in a compatible part of the human anatomy (and specifically the user's outer ear or ear canal or both), including the crus of the helix, cavum concha, cymba concha, intertragic notch, and the outer ear or ear canal or both as will be readily appreciated by the skilled person. As will be readily appreciated by the skilled person, sleeve (1) is designed to make contact with key surfaces of the anti-helix, tragus, anti-tragus, and ear canal In at least one embodiment it is contemplated that body (2) and sleeve (1) are designed with one or multiple grooves that allow the sleeve/body to expand, contract or deform as needed in order to conform a majority of people's ears, as can be seen in FIG. 3.

In some embodiments, it is contemplated that both body (2) and sleeve (1) can be designed with a concave surface area on an outer surface to allow for the outflow of excess photopolymer during insertion of the device into the ear. In some embodiments, it is contemplated that photopolymer may be reintroduced into the ear by applying pressure on the concave surface either manually or with an expandable bladder (3).

Light Source Component Overview

In order to cure photopolymer body (2), a light source (4) can be provided such that body (2) is exposed to the respective type of light source (4) required for curing. As will be readily understood by the skilled person, the type of light source (4) is contingent upon the photopolymer used. Light source (4) may emit, for example visible light, ultraviolet light, fluorescent light, infrared light, blue light, among other segments of spectrum that will be readily understood by the skilled person. However and as will be understood by the skilled person, the application of the light source again varies on implementation.

In at least one embodiment, the typical wavelength utilized for light source (4) is 365 nm. In at least one embodiment, the typical wavelength utilized for light source (4) is 470 nm. However, in other embodiments, the wavelength of light source (4) can be approximately between the range of 265 nm-500 nm.

In at least one embodiment, it is contemplated that the light source is embedded within customizable ear insert (10) such that both light source (4) and body (2) are coupled together. In some embodiments, light source (4) remains within body (2) post curing. It is contemplated that the embedded light source (4) may be of any portable light source including, but not limited to, LED(s), OLED(s), Quantum Dot, fluorescent bulbs, miniature incandescent bulbs, laser diodes, and other types of portable light sources readily understood by the skilled person.

In at least one embodiment, light source (4) can be embedded within customizable ear insert (10) by depositing light source (4) directly on inside of body (2) and/or sleeve (1). In at least one embodiment, affixation of the embedded light source (4) includes depositing light source (4) on flexible or rigid substrate (not shown) which is then installed on inside of sleeve (1) and/or body (2). Depositing, for either direct or indirect implementations, may be enabled by, for example, chemical vapor deposition (CVD), physical vapor deposition (PVD), sputtering, spin coating, inkjet printing, and/or screen printing. In at least one embodiment, light source (4) is a Quantum Dot LED that includes the further step of dispersing within curable polymer resin and stimulating the resin by electric current and/or a light source disposed within customizable ear insert (10).

It is contemplated that light source (4) may be mounted in a number of arrangements, depending on the embodiment, including: on a printed circuit board (15) within housing (11), on a rigid or flexible substrate (not shown) that is affixed to an inner or outer surface of the housing (11), deposited directly on an inner and/or outer surface of housing (11), as required by the instant application of the present invention. It is contemplated that light source (4) may be of any portable light source including, but not limited to, LED(s), OLED(s), Quantum Dot, fluorescent bulbs, miniature incandescent bulbs, laser diodes, and any other suitable type of portable light sources readily understood by the skilled person. Depositing, for either direct or indirect implementations, may be enabled by chemical vapor deposition (CVD), physical vapor deposition (PVD), sputtering, spin coating, inkjet printing, and/or screen printing, among any other techniques that will be readily appreciated by the skilled person.

In at least one embodiment, light source (4) may be attachable to the customizable ear insert and also has the ability to be removed post curing. Light source (4) can be constructed with dimensions such that light source (4) may appear to be embedded into body (2), however post curing, light source (4) can be removed physically from body (2). The types of attachable light sources may be of any portable light source including, but not limited to, LED(s), OLED(s), Quantum Dot, fluorescent bulbs, miniature incandescent bulbs, laser diodes, and other types of portable light sources readily understood by the skilled person.

In at least one embodiment, light source (4) may be utilized externally such that light source (4) may provide curing effect to body (2) while not affixed to body (2) at any time during the deformable state of body (2), or during the forming state of body (2). Light source (4) may be of any arrangement or dimensions as it will only be used as an external component relative to body (2). Suitable types of external light sources can include, but are not limited to, LED(s), OLED(s), Quantum Dot, fluorescent bulbs, miniature incandescent bulbs, halogen lamps, UV generators, infrared generators, spotlights, focal light sources, laser diodes, and other types of portable light sources readily understood by the skilled person.

In at least one embodiment, light source (4) may be utilized externally and may be coupled to the customizable ear insert with optical fibers. In at least one embodiment, the optical fibers may transmit the light from light source (4) throughout body (2). It is contemplated that the optical fibers may be permanently or removably affixed to body (2). The types of external light sources can include, but are not limited to, LED(s), OLED(s), Quantum Dot, fluorescent bulbs, miniature incandescent bulbs, halogen lamps, UV generators, infrared generators, spotlights, focal light sources, laser diodes, and other types of portable light sources readily understood by the skilled person.

In at least one embodiment, light source (4) may be embedded in customizable ear insert (10) and light source (4) may be coupled with optical fibers that are embedded in the customizable ear insert. The embedded light source may be of any portable light source including, but not limited to, LED(s), OLED(s), Quantum Dot, fluorescent bulbs, miniature incandescent bulbs, laser diodes, and other types of portable light sources readily understood by the skilled person. In at least one embodiment, affixation of the embedded light source (4) includes depositing light source (4) on flexible or rigid substrate (not shown) which can then be installed on the inside of sleeve (1), body (2) or housing (11) as required by the needs of the instant application.

In at least one embodiment, specialized semiconductor materials are implemented in connection with light source (2) including, but not limited to, Indium Galium Nitride (InGaN), Gallium Nitride (GaN), and Aluminum Gallium Nitride (AlGaN). These particular materials can provide for emission of ultraviolet light. In some embodiments, it is contemplated that light source (4) may be powered by a number of methods depending on the application of light source (4). In embodiments where light source (4) is external, light source (4) may run on proprietary power sources. In integrated embodiments, light source (4) may utilize power from the user device to power the light source through the communication means (e.g., auxiliary cable, USB cable). In at least one embodiment, the light sources employ voltage and/or current regulating circuits to optimize power consumption. In at least one embodiment, light source (4) can be integrated with embedded batteries (12) for self-sustaining power.

Curing Process

It will be readily understood that the curing process is dependent on the implementation of the type of light source and photopolymer selected. In some embodiments, the curing process utilizes electromagnetic radiation triggering polymerization of the selected photopolymer. In some embodiments, photopolymers consisting of a variety of monomers and oligomers are cross-linked upon exposure to light, forming what is known as a network polymer; effectively constructing a cured network of polymers.

As will be readily understood by the skilled person, the curing process is initiated by a number of mechanisms and responds to a number of various inputs and other modules. Once initiated, the curing process continues for a calculated duration in order to transform body (2) from a first shape, which is deformable and pliable, to a second shape, which is rigid and shape retentive.

In at least one embodiment, the curing process may be pre-configured to cure for a defined duration and has a single cycle for curing. This may be pre-programmed into the embedded circuitry within light source (4).

In at least one embodiment, dependent on configuration, the curing process may last 10 seconds. In other embodiments, dependent on configuration, it is contemplated that the curing process may last 10 minutes, among other arrangements that will be readily contemplated by the skilled person.

In at least one embodiment, body (2) may be constructed from one, or a combination of the following polymers: acrylate, methacrylate, urethane, acrylated urethane, polyester, silicone. In at least one embodiment, it is contemplated that the corresponding LEDs for curing this photocurable polymer emit light in the wavelength of 365 nm-500 nm.

In at least one embodiment, it is contemplated that the initiation of the curing process may be done remotely utilizing a network enabled device. In these embodiments, the device may provide the particular instructions by a communication means to the customizable ear insert, and in turn, the light source implements the instructions given from the device. Further, it is contemplated the device may implement instructions from an Application "App" or a network-based instruction (e.g., through online website calibration, or cloud based service). In these embodiments, it is contemplated that utilizing the online configuration through the device allows for additional parameters to be taken into consideration.

Bladder Implementation

In at least one embodiment and as can be seen in FIG. 1, bladder (3) sits between the inner body and the polymer resin. Further, in some embodiments, it is contemplated that a micro-pump (8) can sit inside the body (2) or housing (11) depending on the arrangement employed. It is also contemplated that micro-pump (8) may be a single or dual direction piezoelectric or electromagnetic diaphragm pump. In the case of an earplug application, micro-pump (8) may be located within the bladder (3).

Bladder (3) may be utilized to expand or contract body (2) based on input that may be given to the bladder (3) utilizing a device with communication means to the ear piece. In this way, it is contemplated that an App can be implemented to control fit utilizing the bladder system.

Bladder (3) may be sealed and acted upon by a means for controlling the temperature of the contained gas which can include but is not limited to atmospheric air. The temperature control apparatus can comprise, for example, a resistive heating element or a peltier element, among other arrangements that will be readily understood by the skilled person. In these embodiments, the thermal expansion of the gas within bladder (3) will serve to expand or contract body (2). In some embodiments, the heating and cooling elements can be contained in the bladder (3), contained in body (2), on the surface of sleeve (1), on the surface of the inner body, on the surface of the housing (11), or in the housing (11) with a means for being in fluid communication with the bladder (3) depending on the needs of the instant application.

It is contemplated that in some embodiments bladder (3) may sit between the housing (11) and the sleeve (1) or body (2). Further, in some embodiments bladder (3) can consist of one or multiple pockets that are integrated into the form of the sleeve (1).

Sleeve Implementation

In at least one embodiment, sleeve (1) is implemented for customized ear insert (10) such that sleeve (1) is applied on the outer surface of body (2), and/or body (2) and light source (4) configuration, depending on the specific embodiment.

It is contemplated in at least one embodiment that sleeve (1) can physically function as a cover material for the body. Further, it is contemplated that sleeve (1) may be constructed of any material depending on its application. For headphone applications the material used must allow for the output from the underlying speaker component (6) to function with a pre-defined acceptable audio quality.

In at least one embodiment the construction of the sleeve (1) may be any material which allows for conformability to the underlying body (2) and provides the requisite elasticity. The material for sleeve (1) may include, but is not limited to, foam, silicone, cotton, wool, rubber, polymer, plastic, synthetic materials, natural materials, latex, thermoplastic vulcanizate, thermoplastic elastomer, thermoplastic polyurethane, and over-molded combination of multiple materials.

In at least one embodiment, it is contemplated that sleeve (1) can be affixed to body (2), while in other embodiments, it is contemplated that sleeve (1) is removable from body (2).

In some embodiments it is contemplated that select inner or outer surfaces of sleeve (1) may be coated with a reflective material in order to assist light propagation through the photopolymer.

In some embodiments, it is contemplated that a coating may be applied to select areas of the inner and/or outer surface of sleeve (1) in order to block or reduce unintended/undesired light exposure of the photopolymer. The coating may block all light transmission or select frequency bands in the visible, infrared, and/or UV spectrums.

In some embodiments, it is contemplated that an additive may be blended in to select areas of the sleeve material in order to block or reduce unintended/undesired light exposure of the photopolymer. The coating may block all light transmission or select frequency bands in the visible, infrared, and/or UV spectrums.

Mechanisms for Fit of Ear Insert

It is contemplated that the fit of the ear insert may be configured utilizing a variety of mechanisms. In at least one embodiment, transducers (19) are implemented within body (2) such that various metrics can be measured as the ear insert is worn by a user. The transducers (19) are of sufficient dimension such that they are embedded in body (2) or affixed to the sleeve (1). In at least one embodiment, the transducers (19) are powered by a communication means.

In at least one embodiment, it is contemplated that the transducers (19) are adapted to send data wirelessly to receivers. It is contemplated that the receivers may be any device configured to receive the transmission from the transducers (19). For example, in at least one embodiment, the device may be a network enabled device. In some embodiments, the device receiving the data, computes the ideal pressure based on a variety of factors including, but not limited to, user's personal information input, the health and safety regulations for auditory devices, any other guidelines readily understood by the skilled worker. The computed adjustment is sent back to the transducers (19), either wirelessly or through communication means, to implement the computed adjustment for desired configuration.

In at least one embodiment, it is contemplated that the transducers (19) are pressure sensors. The pressure sensors may be of any type of pressure sensor, including but not limited to strain gauges. The pressure sensors measure the pressure of the ear pushing against the body of the ear insert. In some embodiments, the data is recorded and stored within the sensor mechanism. The transfer of the data may occur wirelessly when a compatible device is within range, or alternatively can wait until a physical connection is made using a conventional communication means such as USB.

In at least one embodiment, an App is implemented on a device whereby the configuration for pre-configured pressures can be applied. In some embodiments, a calibration option may exist on the App allowing user configuration of pre-configured pressures. Alternatively, a calibration option may exist on the App allowing for the user of the ear insert to adjust the pressure of the body prior to photopolymer body curing. In at least one embodiment, the App is operable as the photopolymer body (2) is curing. The user may provide feedback to the App and customize the pressure of body (2) against their ear in real time. In some embodiments, the user may also compare his desired fit against recommended and/or pre-set configuration for pressure recommended by other users, manufacturers, medical practitioners, and/or industry experts.

In at least one embodiment, the calibration receives feedback from one or more feedback modules via a communication means. For example, the feedback modules could be one or more microphones (9) which are connected through a USB cable to the user device. Feedback modules could be one or more microphones embedded in specific locations in the earphones and communicate with user device via wireless integrated circuit. The information sent from microphones (9) to the user device is then compared to a set of pre-set values for calibration. These values could be part of a network-enabled database which the user device is connected to. In such a way, the information from microphones (9) is sent to the database for a comparison to determine what manipulation is required for the fit of the customized ear piece based on the feedback from the one or more microphones (9). The user then follows instructions provided by the user device and the test then iterates until the microphone feedback matches the calibration pre-sets in the database to a certain threshold.

Cavity Embodiment

In at least one embodiment, a cavity (5) is pre-constructed into body (2) of the customizable ear insert (10). Cavity (5) may serve any number of purposes depending on instant application of customizable ear insert (10). In at least one embodiment, cavity (5) serves to allow for the insertion of hearing system components. In at least one embodiment, cavity (5) serves to allow for the insertion of transducers. In at least one embodiment, the shape and configuration of cavity (5) serves to allow for a desired audial response profile.

In at least one embodiment, cavity (5) is constructed with a mechanism allowing for attachment of one or more hearing system components, or transducers. The attachments can be attached and removed and interchanged at the will of the user.

In at least one embodiment, cavity (5) is constructed such that the implementation of one or more hearing system components or transducers is affixed to the cavity (5) and integrated during fabrication, or thereafter, such that the components are not detachable.

Microphones Embodiment

In at least one embodiment, cavity (5) is configured to house one or more microphones (9). As will be readily appreciated by the skilled person, the microphones may serve any number of purposes depending on application of customizable ear insert (10).

In at least one embodiment, microphone (9) is utilized for calibration of customizable ear insert (10) by detecting, for example, air flow, wind speed or ambient environmental sound. In other embodiments, microphone (9) may be configured such that one microphone is on the exterior of the body while one microphone is on the inner section of body (2) (e.g., the side of the body with a potential speaker configuration). Each microphone may send audial information to the device by a communication means. The device may determine various metrics such as "leakage" of air between customizable ear insert (10) and the user's ear. In this case, the microphone may be used to calibrate the fit of customizable ear insert (10) within the user's ear. The interface between the microphone and the information provided may be conducted through an App on the user's device.

In at least one embodiment, it is contemplated that one microphone measures sound pressure level on the exterior of the ear insert and a second microphone measures sound pressure level at the proximal tip of the ear insert inside the ear. In these embodiments, the noise level reduction, which can be measured in decibels, will be used to determine when an adequate seal has been achieved.

In at least one embodiment, the calibration utilizing the microphones may be utilized to calibrate the fit of customizable ear piece (10) prior to the curing of customizable ear insert (10). The microphones may be used to measure bypass sound pressure levels at predetermined locations on body (2). In this way, the App utilizes the information sent by the microphones in order to map the correct pressure to ensure the optimal spatial fit of customizable ear insert (10).

In at least one embodiment, the one or more microphone (9) may be utilized to provide noise cancelling of ambient sound utilizing techniques readily understood by a person skilled in the art.

Speakers Embodiment

In at least one embodiment, cavity (5) is configured to house one or more speakers (6) to provide audial output. In at least one embodiment, speakers (6) can be attached to the device (affixed or detachable) such that speakers (6) are fully integrated within the mold of body (2) to provide audial output to the user.

In at least one embodiment, speakers (6) are utilized for calibration of customizable ear insert (10) by providing audial tests to the user based on environmental conditions. The interface between speakers (6) and the information provided may be conducted through an App on the user's device. The App may contain a simulation of ideal audial response and requisition the user to complete a survey regarding the response and clarity of audio based on user action.

In at least one embodiment, speakers (6) are utilized for calibration by producing audial tones at specific frequencies and sound pressure levels. In embodiments where microphones are provided on the exterior of body (2) may be used to measure the presence of these tones. The noise level reduction, measured in decibels, will therefore be used to determine when an adequate seal has been achieved.

It is obvious that the foregoing embodiments of the invention are examples and can be varied in many ways. Such present or future variations are not to be regarded as a departure from the spirit and scope of the invention, and all such modifications as would be obvious to one skilled in the art are intended to be included within the scope of the following claims.

What is claimed is:

1. A customizable ear insert for insertion into an outer ear and an ear canal of a user, comprising:
    a body formed of a photocurable polymer which has a first shape that is deformable and pliable;
    a light source configured to emit radiation to cure the photocurable polymer, wherein the light source is positioned within a housing;
    a sleeve that surrounds at least a portion of the body, wherein the sleeve comprises an elastic material; and
    an integrated circuit positioned within the housing, the integrated circuit configured for wireless communication and configured to enable the emission of the radiation from the light source, and
        when a portion of the sleeve and the body are positioned within the ear canal of the user and exposed to the radiation emitted from the light source, the sleeve and the body form a shape-retentive second shape adapted to conform to a portion of outer ear of the user.

2. The customizable ear insert of claim 1, further comprising an attachment means, wherein the attachment means allows the sleeve and body to be mechanically and removably connected to the housing.

3. The customizable ear insert of claim 2, wherein the attachment means comprises a snap fit.

4. The customizable ear insert of claim 1, wherein the housing further comprises embedded batteries that are coupled to the light source.

5. The customizable ear insert of claim 1, wherein the sleeve is affixed to the body.

6. The customizable ear insert of claim 1, wherein the elastic material is selected from the group consisting of thermoplastic polyurethane and silicone.

7. The customizable ear insert of claim 1, further comprising one or more transducers that are embedded within the body, and configured to measure pressure applied to the body.

8. The customizable ear insert of claim 7, wherein the one or more transducers comprise strain gauges.

9. The customizable ear insert of claim 1, further comprising a cavity located within the housing.

10. The customizable ear insert of claim 9, wherein the cavity is adapted to receive at least one speaker.

11. The customizable ear insert of claim 9, wherein the cavity is adapted to receive at least one microphone, wherein the at least one microphone is a first microphone located in the housing.

12. The customizable ear insert of claim 11, wherein the at least one microphone includes the first microphone and a second microphone located in the body.

13. The customizable ear insert of claim 12, wherein the first microphone and the second microphone are configured to detect at least one of:
    audial leakage from the ear canal to an external environment and audial leakage from the external environment to the ear canal.

14. The customizable ear insert of claim 11, wherein the first microphone is adapted to fluidly communicate with the outer ear and an external environment by way of a sound bore.

15. A customizable ear insert for insertion into an outer ear and an ear canal of a user, comprising:
    a body formed of a photocurable polymer which has a first shape that is deformable and pliable;
    a light source configured to emit radiation to cure the photocurable polymer, wherein the light source is positioned within a housing;
    a sleeve that surrounds at least a portion of the body; and
    an integrated circuit positioned within the housing, the integrated circuit configured for wireless communication and configured to enable the emission of the radiation from the light source;
    wherein when positioning a portion of the sleeve and the body within the outer ear of the user and exposing the portion of the sleeve and the body to the radiation emitted from the light source, the sleeve and the body form a shape-retentive second shape adapted to conform to a portion of the outer ear of the user.

16. The customizable ear insert of claim 15, further comprising an attachment means, wherein the attachment means allows the sleeve and body to be mechanically and removably connected to the housing.

17. The customizable ear insert of claim 15, wherein the housing comprises embedded batteries that are coupled to the light source.

18. A customizable ear insert for insertion into an outer ear and an ear canal of a user, comprising:
    a body formed of a photocurable polymer which has a first shape that is deformable and pliable;
    a light source configured to emit radiation that will cure the photocurable polymer, wherein the light source is positioned within a housing;
    a sleeve that surrounds at least a portion of the body, wherein the sleeve comprises an elastic material; and
    an attachment means;
    wherein the attachment means allows the sleeve and body to be mechanically and removably connected to the housing, and
        when a portion of the sleeve and the body are positioned within the ear canal of the user and exposed to the radiation emitted from the light source, the sleeve and the body form a shape-retentive second adapted to conform to a portion of the ear canal of the user.

19. The customizable ear insert of claim 18, further comprising a communication means that is configured to receive power from an external device to enable the emission of the radiation from the light source.

20. The customizable ear insert of claim 18, wherein the housing further comprises embedded batteries that are configured to provide power to the light source.

* * * * *